(12) United States Patent
Sander

(10) Patent No.: US 10,390,842 B2
(45) Date of Patent: Aug. 27, 2019

(54) GEARED INSTRUMENT FOR TIBIAL STEM REAMING OR REMOVAL

(71) Applicant: Wright Medical Technology, Inc., Memphis, TN (US)

(72) Inventor: Elizabeth J. Sander, Memphis, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 851 days.

(21) Appl. No.: 14/403,772

(22) PCT Filed: Aug. 19, 2014

(86) PCT No.: PCT/US2014/051654
§ 371 (c)(1),
(2) Date: Nov. 25, 2014

(87) PCT Pub. No.: WO2016/028270
PCT Pub. Date: Feb. 25, 2016

(65) Prior Publication Data
US 2016/0051267 A1   Feb. 25, 2016

(51) Int. Cl.
*A61B 17/16*   (2006.01)
*F16H 1/14*    (2006.01)
*F16H 1/16*    (2006.01)

(52) U.S. Cl.
CPC ...... *A61B 17/1682* (2013.01); *A61B 17/1624* (2013.01); *F16H 1/14* (2013.01); *F16H 1/145* (2013.01); *F16H 1/16* (2013.01)

(58) Field of Classification Search
CPC ...... B23B 45/06; B25B 17/00; A61B 17/1682
(Continued)

(56) References Cited

U.S. PATENT DOCUMENTS

| 755,078 A * | 3/1904 | Trumbull ......... B23B 45/06 81/34 |
| 1,530,138 A * | 3/1925 | Rush ........... B23B 45/06 81/124.1 |

(Continued)

FOREIGN PATENT DOCUMENTS

| JP | H06-086784 A | 3/1994 |
| JP | H09-019437 A | 1/1997 |
| JP | 2005118415 A | 5/2005 |

OTHER PUBLICATIONS

Supplementary European Search Report issued in connection with corresponding European patent application No. 14843156.2, dated Aug. 9, 2016, 7 pages.
(Continued)

*Primary Examiner* — David W Bates
(74) *Attorney, Agent, or Firm* — Duane Morris LLP

(57) ABSTRACT

The present subject matter relates to a geared instrument. The geared instrument is configured to translate rotation about a first axis to rotation about a second axis. The geared instrument comprises a handle configured to rotate about the first axis. A translation gear is configured to couple to the handle. A stem is coupled to the translation gear and rotates in unison with the translation gear. The translation gear is configured to translate the rotation of the handle about the first axis to rotation of the stem about the second axis. The stem is configured to couple to a modular head.

4 Claims, 9 Drawing Sheets

(58) Field of Classification Search
USPC .................................................. 81/57.29, 34
See application file for complete search history.

(56) References Cited

U.S. PATENT DOCUMENTS

| | | | | | |
|---|---|---|---|---|---|
| 1,575,953 | A | * | 3/1926 | Toorks | B23Q 5/045 408/124 |
| 1,579,818 | A | * | 4/1926 | Kennedy | B25B 17/00 81/437 |
| 1,705,384 | A | * | 3/1929 | Wikander | B23B 45/06 408/137 |
| 1,741,507 | A | * | 12/1929 | Orazio | B23B 45/06 279/155 |
| 1,799,393 | A | * | 4/1931 | Rylander | B23B 45/06 475/270 |
| 2,042,376 | A | * | 5/1936 | Balga | B25B 15/00 279/50 |
| 2,102,929 | A | * | 12/1937 | Wallace | B23B 45/06 279/37 |
| 2,701,490 | A | * | 2/1955 | Griparis | B25B 17/00 73/862.26 |
| 2,754,864 | A | * | 7/1956 | Elsy | B23B 51/0426 408/119 |
| 2,800,821 | A | * | 7/1957 | Fruscella | B25B 13/463 81/60 |
| 3,733,936 | A | * | 5/1973 | Flynn | B25B 17/00 81/57.29 |
| 3,843,143 | A | * | 10/1974 | Laxson | B23B 45/06 279/14 |
| 4,311,072 | A | * | 1/1982 | Hudgins | B25B 13/467 81/476 |
| 4,455,896 | A | * | 6/1984 | Holmes | B25B 13/461 81/57.26 |
| 4,517,861 | A | * | 5/1985 | Stemberger | B25B 17/00 81/57.29 |
| 4,645,388 | A | * | 2/1987 | Abrahamsen | B23B 45/003 173/216 |
| 4,680,994 | A | * | 7/1987 | Singleton | B25B 17/00 81/57.29 |
| 4,813,308 | A | * | 3/1989 | Petrus | B25B 13/481 81/57.29 |
| 4,907,476 | A | * | 3/1990 | Singleton | B25B 17/00 81/57.29 |
| 5,013,317 | A | | 5/1991 | Cole et al. | |
| 5,098,293 | A | | 3/1992 | Loeoef et al. | |
| 5,471,898 | A | * | 12/1995 | Forman | B25B 17/00 81/57.13 |
| 6,009,776 | A | * | 1/2000 | Warren | B25B 13/467 81/57.13 |
| 6,047,616 | A | * | 4/2000 | Ochiai | B25B 13/467 81/57.13 |
| 6,112,621 | A | * | 9/2000 | Ochiai | B25B 17/00 81/57.13 |
| 7,100,476 | B1 | * | 9/2006 | Feit | A61B 17/8875 433/114 |
| 7,534,246 | B2 | | 5/2009 | Reiley et al. | |
| 7,588,573 | B2 | * | 9/2009 | Berry | A61F 2/44 606/53 |
| 8,707,831 | B2 | * | 4/2014 | Palmer | B25B 13/463 74/810.1 |
| 9,629,730 | B2 | * | 4/2017 | Reiley | A61F 2/4202 |
| 2003/0225411 | A1 | | 12/2003 | Miller | |
| 2005/0229752 | A1 | * | 10/2005 | Nickipuck | B25B 23/0014 81/177.75 |
| 2010/0262150 | A1 | * | 10/2010 | Lian | A61B 17/15 606/87 |
| 2010/0268235 | A1 | | 10/2010 | Teichmann | |
| 2011/0218542 | A1 | * | 9/2011 | Lian | A61B 17/15 606/88 |
| 2012/0130376 | A1 | * | 5/2012 | Loring | A61B 17/025 606/80 |
| 2012/0271314 | A1 | * | 10/2012 | Stemniski | A61B 17/15 606/87 |
| 2012/0297939 | A1 | * | 11/2012 | Spata | B25B 13/463 81/478 |
| 2013/0046313 | A1 | * | 2/2013 | Lian | A61B 17/92 606/99 |
| 2013/0325012 | A1 | | 12/2013 | Piferi et al. | |
| 2015/0134071 | A1 | * | 5/2015 | Luna | A61B 17/15 623/21.18 |
| 2018/0177513 | A1 | * | 6/2018 | Stemniski | A61B 17/15 |

OTHER PUBLICATIONS

Patent Examination Report issued in connection with corresponding Australian patent application No. 2014318027, dated Jun. 28, 2016, 3 pages.

First Office Action issued in connection with corresponding Japanese patent application No. 2016-517385, dated Jan. 29, 2017, 4 pages.

Korean Intellectual Property Office, International Search Report and Written Opinion for PCT/US2014/051654, dated May 13, 2015, pp. 1-16.

* cited by examiner

GEARED INSTRUMENT FOR TIBIAL STEM REAMING OR REMOVAL

CROSS REFERENCE TO RELATED APPLICATIONS

This application is a national phase entry under 35 U.S.C. 371 of international patent application No. PCT/US14/51654, the entirety of which is incorporated herein by reference.

FIELD OF THE INVENTION

This disclosure generally relates to systems and methods for orthopedic surgery. More particularly, this disclosure relates to systems and methods for tibial stem reaming or removal.

BACKGROUND

The ankle is a joint that acts much like a hinge. The joint is formed by the union of three bones. The ankle bone is the talus. The top of the talus fits inside a socket that is formed by the lower end of the tibia and the fibula, the small bone of the lower leg. Arthritis, bone degeneration, and/or injury can cause ankle joint deterioration resulting in pain, reduced range of motion, and decreased quality of life. In many cases, physicians are recommending ankle replacement surgery with an implant as an option.

In traditional ankle replacements, multiple incisions are made to provide access to the ankle. An anterior incision is made lateral of the tibia, with care taken to avoid the anterior tendons. The anterior incision exposes the tibia, talus, and a portion of the midfoot. In some embodiments, the anterior incision is approximately 125 mm long, however it will be recognized that the incision can be greater or less than 125 mm. One or more additional incisions are made, for example, on the bottom of the foot, to provide access to the tibia canal to allow an implant stem hole to be formed in the tibia. The additional incisions increase recovery time and increase the chance of infection after surgery.

SUMMARY

The present subject matter generally relates to a geared instrument. The geared instrument is configured to translate rotation about a first axis to rotation about a second axis. The geared instrument comprises a handle configured to rotate about the first axis. A translation gear is configured to couple to the handle. A stem is coupled to the gear and rotates in unison with the gear. The translation gear is configured to translate the rotation of the handle about the first axis to rotation of the stem about the second axis. The stem is configured to receive a modular head.

In various embodiments, a surgical system comprising a geared instrument and a modular head is disclosed. The geared instrument is configured to translate rotation about a first axis to rotation about a second axis. The geared instrument comprises a handle configured to rotate about the first axis. A translation gear is configured to couple to the handle. A stem is coupled to the gear and rotates in unison with the gear. The translation gear is configured to translate the rotation of the handle about the first axis to rotation of the stem about the second axis. The modular head is configured to detachably couple to the stem such that rotation of the stem rotates the modular head.

In various embodiments, a method of using a geared instrument for an ankle replacement is disclosed. The method comprises locating a geared instrument at a prepared ankle joint. The instrument comprises a handle configured to rotate about the first axis. A translation gear is configured to couple to the handle. A stem is coupled to the gear and rotates in unison with the gear. The translation gear is configured to translate the rotation of the handle about the first axis to rotation of the stem about a second axis. The method further comprises releasably coupling a modular head to the stem such that the modular head rotates in unison with the stem. The handle is coupled to the gear and rotated about the first axis. Rotation of the handle about the first axis rotates the stem and the modular head, through the translation gear, about the second axis. Rotation of the modular head allows the modular head to perform a surgical procedure.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
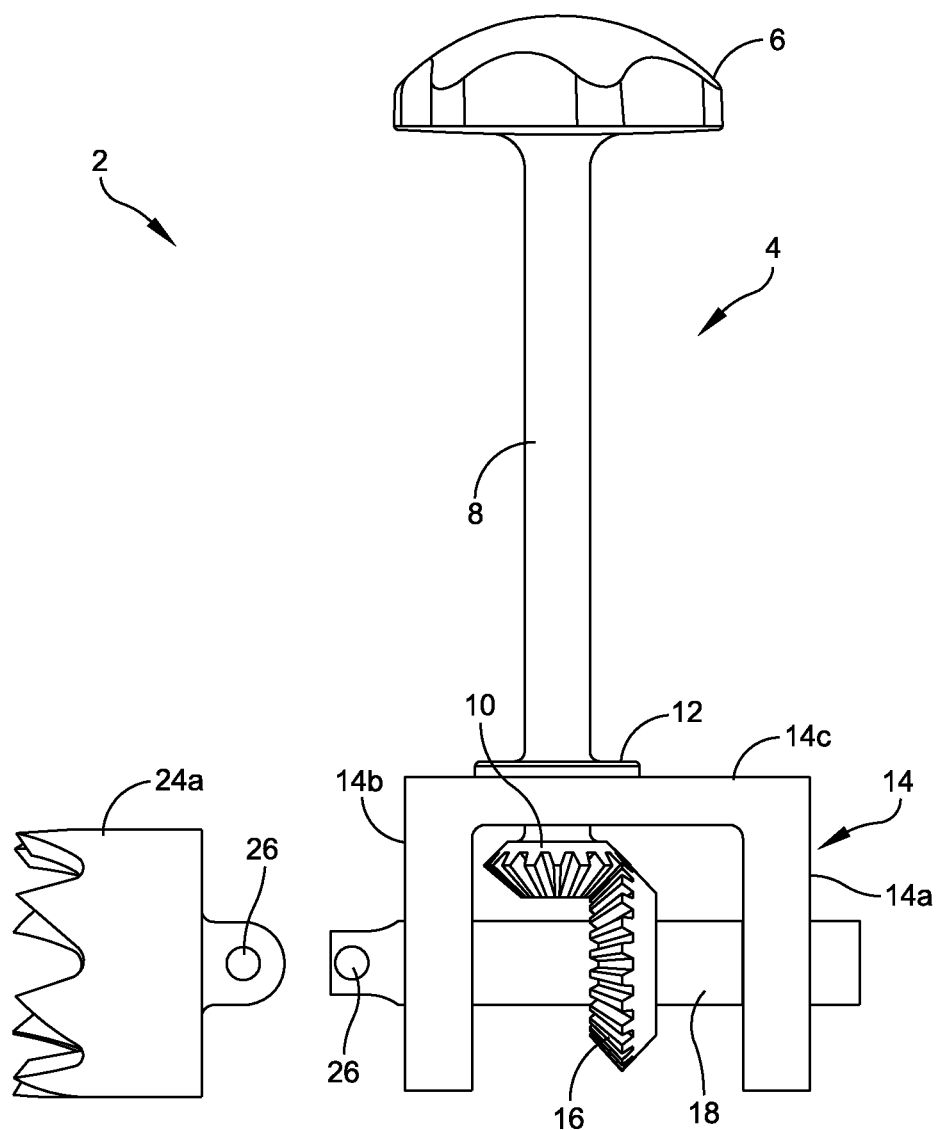
FIG. 1 illustrates one embodiment of a geared instrument for stem reaming and removal.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a geared instrument for stem reaming and removal. The geared instrument generally comprises a handle configured to rotate about a first axis. The handle couples to a gear. A stem extends longitudinally from the gear. The gear is configured to translate rotation of the handle about the first axis to rotation of the stem about a second axis. The stem comprises a modular connection configured to receive a modular head.

FIG. 1 illustrates one embodiment of a geared instrument 2 for stem reaming and removal. The geared instrument 2 comprises a handle 4. The handle 4 comprises a gripping portion 6 and a shaft 8 longitudinally on a first axis from the gripping portion 6. In some embodiments, the gripping portion 6 may be replaced by a connection mechanism for coupling the handle 4 to an instrumented and/or mechanical drive. The connection mechanism may be replaced by any suitable connection type such as, for example, threaded connection, a press-fit connection, and/or any other suitable connection. A handle gear 10, such as, for example a pinion, is located at the distal end of the shaft 8. In some embodiments, a stop ring 12 is coupled to the shaft 8 proximally of the handle gear 10. The handle is rotatable about the longitudinal axis of the shaft 8.

The handle 4 is received within a housing 14. The housing 14 comprises at least two side walls 14a, 14b and a top wall 14c. In other embodiments, the housing 14 may comprise a circular housing, a tubular housing, and/or any other suitable housing. A top opening (not shown) is formed in the top wall 14c. The top opening is sized and configured to receive the handle gear 10 and a portion of the shaft 8 therein. The stop ring 12 is sized and configured to prevent the handle 4 from being inserted into the housing 14 beyond a predetermined point. Additionally, a portion of the shaft 8 may be captured in the housing 14 to prevent the shaft 8 from being accidentally removed from the housing 14. A translation gear 16 is located within the housing 14. The translation gear 16 is configured to couple to the handle gear 10. The translation gear 16 may comprise any suitable gear such as, for example, a bevel gear, a worm gear, a spiral bevel gear, a hypoid gear, and/or a crown gear. A stem 18 (or axle) extends through the translation gear 16. The housing 14 comprises lateral openings formed in the side walls 14a, 14b. In some embodiments, the housing 14 comprises an open housing which allows access to the translation gear 16 and the stem 18 for cleaning and sterilization. In some embodiments, the housing 14 comprises a closed housing. The stem 18 extends longitudinally along a second axis from a first side wall 14a of the housing 14, through the translation gear 16, and through the lateral opening formed in the second side wall 14b. The stem 18 is coupled to the translation gear 16. The translation gear 16 and the stem 18 are rotatable about the second axis.

When the handle 4 is inserted into the housing 14, the handle gear 10 couples to the translation gear 16. For example, in some embodiments, the handle gear 10 comprises a pinion and the translation gear 16 comprises a bevel gear configured to couple to the pinion. The translation gear 16 translates rotation of the handle 4 about the first axis to rotation of the stem 18 about the second axis. In some embodiments, the first axis and the second axis are perpendicular. In some embodiments, rotation of the handle 4 may comprise a one-to-one ratio with rotation of the stem 18. In other embodiments, the ratio of rotation of the handle 4 to the stem 18 may be greater or less than one.

Figure 2:
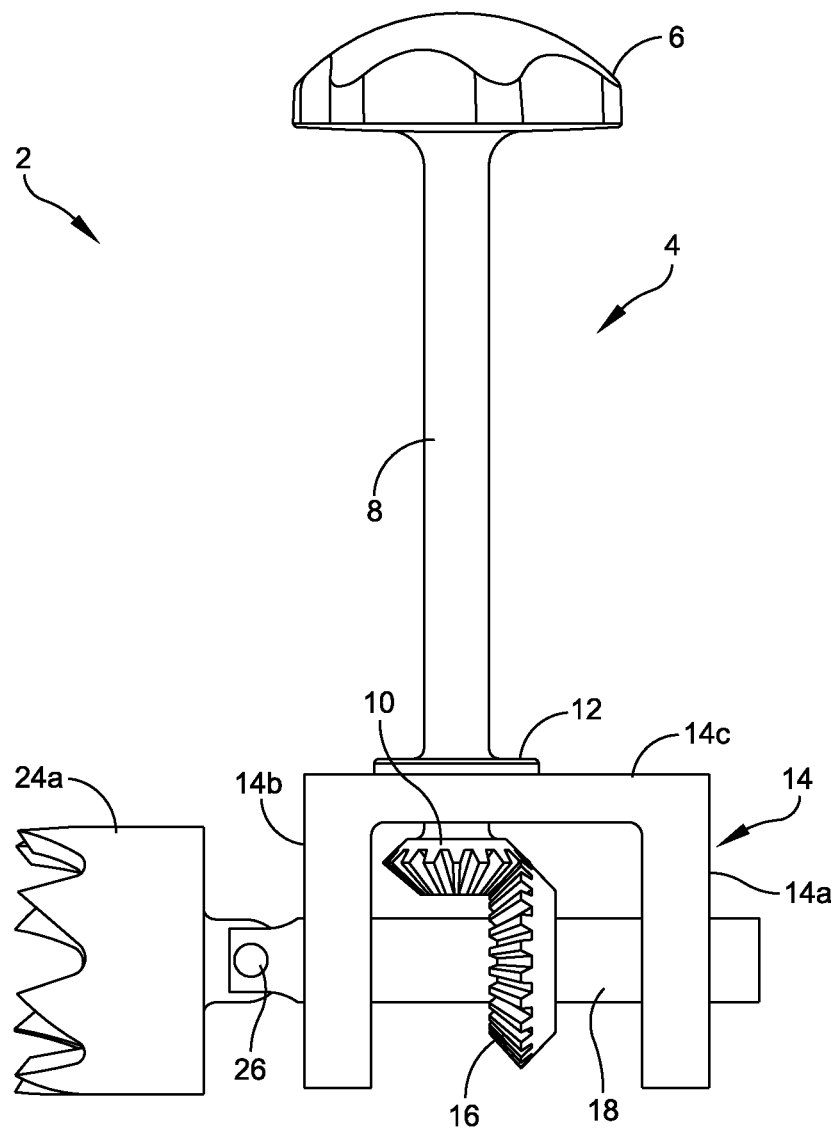
FIG. 2 illustrates the geared instrument of FIG. 1 having a modular head coupled to a stem.

The stem 18 comprises a modular connection 26. The modular connection 26 is configured to couple a modular head 24 to the stem 18. The modular connection 26 may comprise, for example, a hinged connection, a fixed connection, a slideable connection, and/or any other suitable connection. The modular head 24 is coupled to the stem 18 such that the modular head 24 rotates in unison with the stem 18. Rotation of the handle 4 about the first axis rotates the stem 18 and the modular head 24 about the second axis. Rotation of the modular head 24 allows one or more surgical procedures to be performed without needing direct axial access to a bone. The modular head 24 may comprise, for example, a drill bit, a reamer, a stem remover, and/or any suitable instrument. FIG. 2 illustrates the geared instrument 2 having the modular head 24 coupled to the stem 18.

Figure 3:
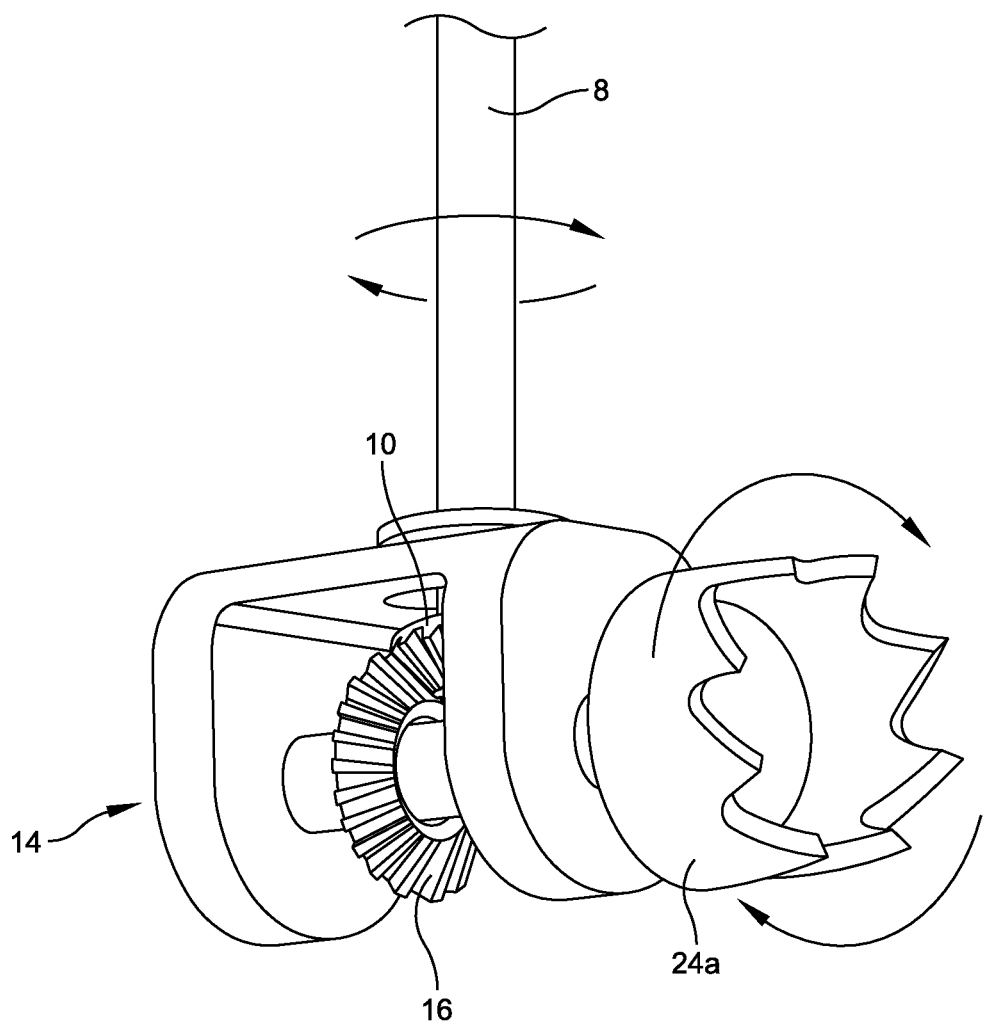
FIG. 3 illustrates translation of rotation about a first axis defined by a handle to rotation about a second axis defined by a stem.

FIG. 3 illustrates translation of rotation about the first axis to rotation about the second axis. The handle 4 may be rotated about the first axis by, for example, a clinician gripping the gripping portion 6. The handle 4 may be rotatable in a first direction and/or a second direction. Rotation of the handle 4 about the first axis rotates the handle gear 10 about the first axis. The handle gear 10 is coupled to the translation gear 16. The handle gear 10 rotates the translation gear 16 about the second axis. The stem 18 is coupled to the translation gear 16 and rotates about the second axis in unison with the translation gear 16. Rotation of the stem 18 rotates the modular head 24a coupled thereto. Rotation of the modular head 24a allows one or more surgical procedures to be performed without direct axial access to a surgical site.

The geared instrument 2 is configured to facilitate one or more surgical procedures. For example, in some embodiments, the geared instrument 2 is sized and configured to facilitate an ankle resectioning and/or replacement. The geared instrument 2, and specifically the housing 14, is configured to fit through an anterior incision formed during an ankle resectioning and/or replacement. The use of the geared instrument 2 eliminates the need for additional incisions providing axial access to the tibial canal. Instead, the housing 14 fits within the ankle joint through the anterior incision and allows a channel to be formed in the tibial canal from the anterior incision. The housing 14 is free-floating within the ankle joint to allow the housing 14 to be positioned as needed for performing one or more procedures.

Figure 13:
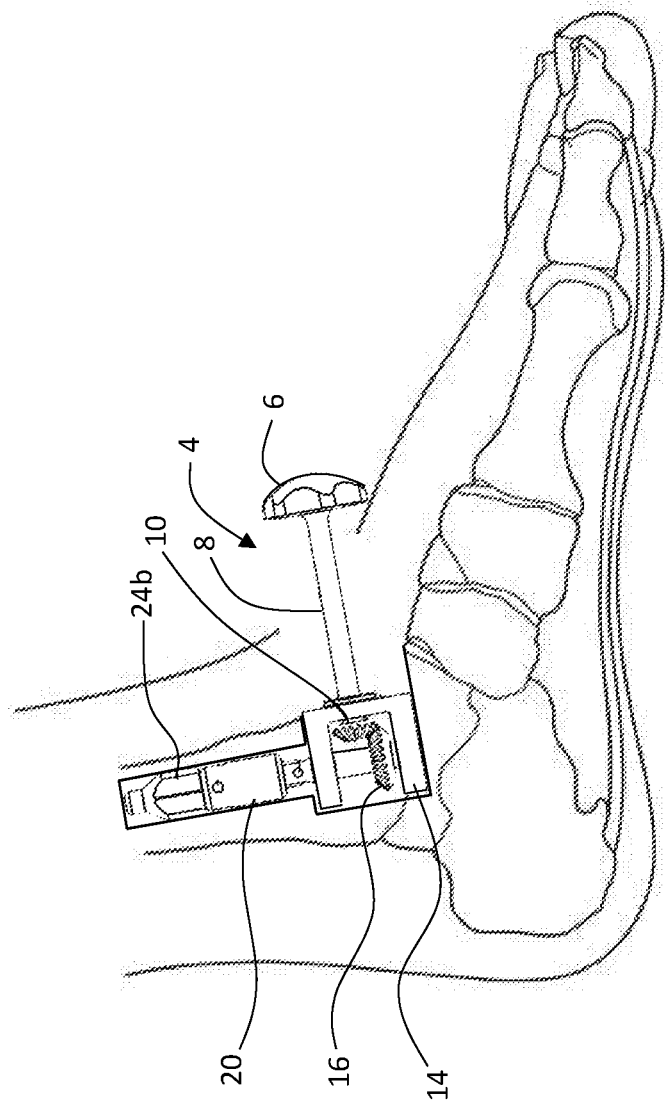
FIG. 13 illustrates the geared instrument of FIG. 4 located within an ankle joint.

The modular connection 26 of the stem 18 allows the modular head 24 to be switched without needing to remove the geared instrument 2 from the patient. For example, in one embodiment, the geared instrument 2 is sized and configured for an ankle replacement. The geared instrument 2, and specifically the housing 14, is configured to fit through an anterior incision in a patient and be located within an ankle joint, as shown in FIG. 13. A first modular head, such as, for example, a drill bit (see FIG. 9) is coupled to stem 18 by the modular connection 26. The handle 4 is inserted through the top opening of the housing 14 to couple the handle gear 10 to the translation gear 16. The handle 4 is rotated about the first axis, rotating the drill bit about the second axis to drill a pilot hole into the tibia. After the first procedure is performed, the handle 4 is rotated about the first axis in an opposite direction to withdraw the drill bit. The first modular head is detached from the stem 18 and a second modular head is attached to the stem 18 by the modular connection 26. The second modular head may comprise, for example, a reamer (see FIG. 8). Once the reamer is coupled to the stem 18, the handle 4 is rotated in the first direction to ream the pilot hole in the tibia to a channel sized and configured to receive an implant therein. Those skilled in the art will recognize that additional and/or alternative modular heads may be coupled to the stem 18. Modular heads may be provided to the surgical site as needed and/or may be inserted when the geared instrument 2 is inserted and switched during a surgical procedure.

Figure 4:
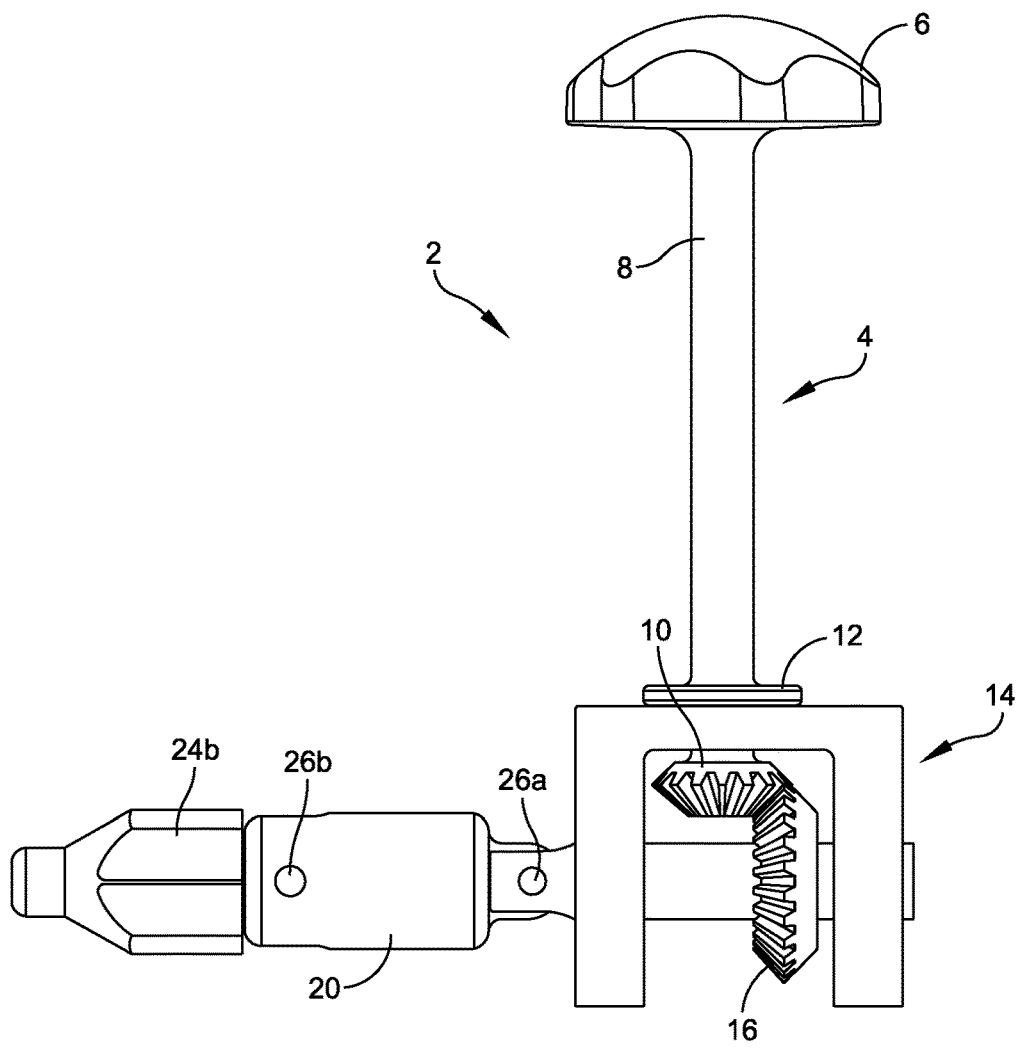
FIG. 4 illustrates the geared instrument of FIG. 1 having a modular extender coupled to the stem and a second modular head coupled to the modular extender.
Figure 5:
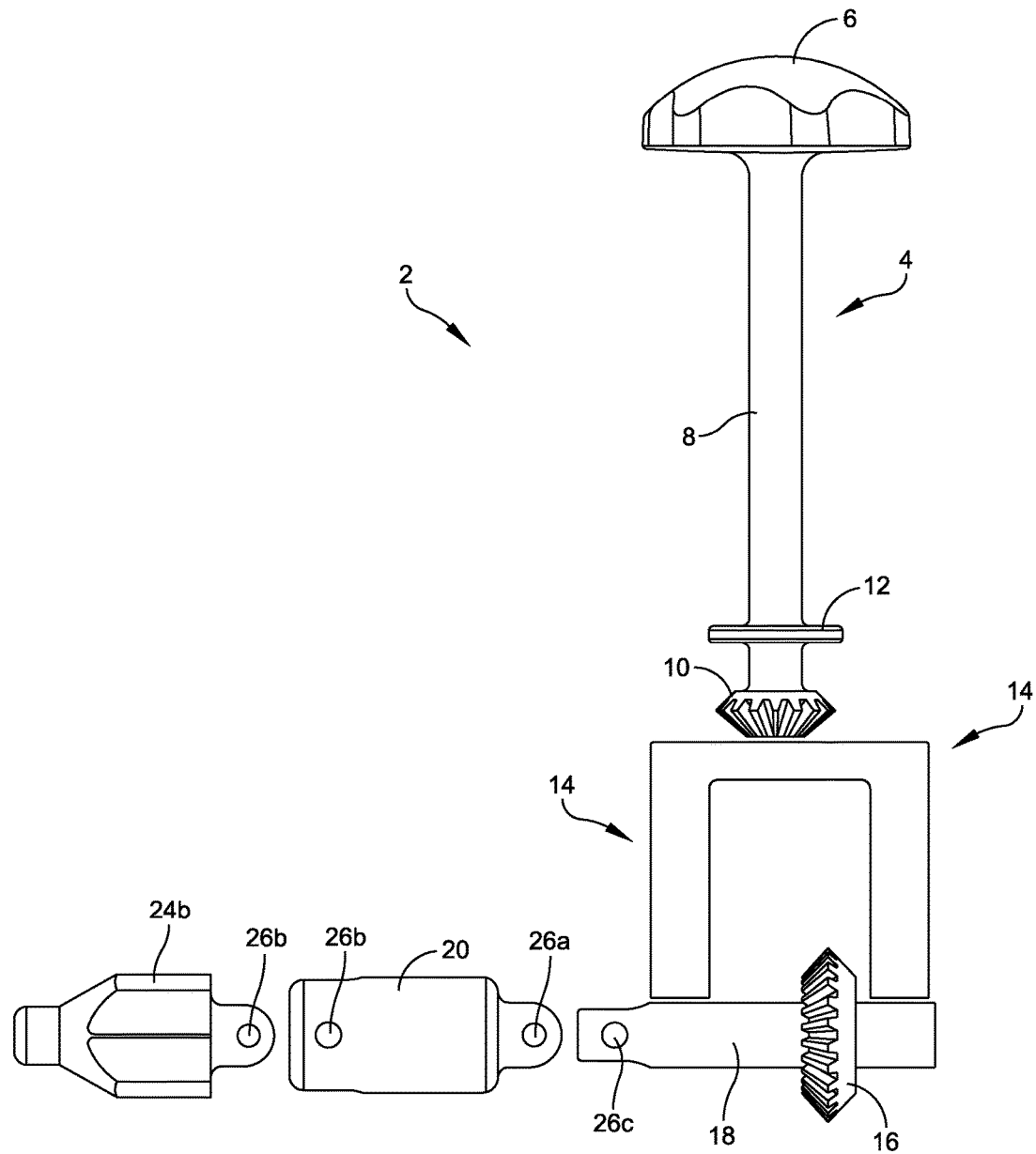
FIG. 5 illustrates an exploded view of the geared instrument of FIG. 4.

FIG. 4 illustrates one embodiment of the geared instrument 2 having a modular extender 20 coupled between the stem 18 and a second modular head 24b. At a first end, the modular extender 20 comprises a modular connection 26a configured to couple to the modular connection 26 of the stem 18. At a second end, the modular extender 20 comprises a modular connection 26b configured to couple to the modular connector of the modular head 24b. The first end and the second end are coupled by a longitudinal body. The modular extender 20 allows the modular head 24b to reach deeper sections of a bone. The modular extender 20 is rotationally coupled to the stem 18 and the modular head 24 such that rotation of the stem 18 results in rotation of the modular extender 20 and the modular head 24. FIG. 5 illustrates an exploded view of the geared instrument 2 having a modular extender 20 coupled to the stem 18.

Figure 6:
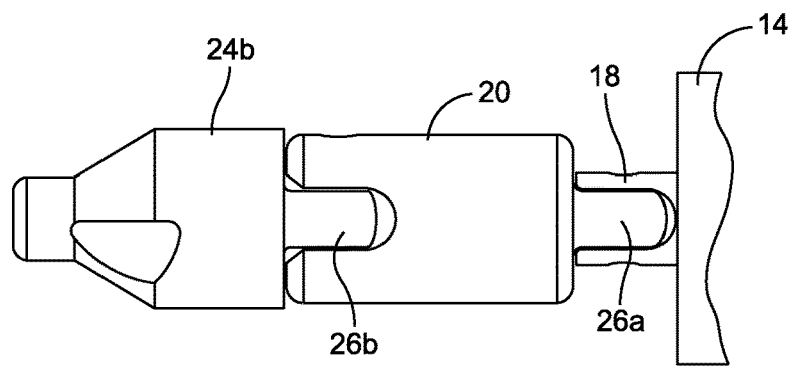
FIG. 6 illustrates a view of the modular connections between the stem, modular extender, and the modular head.
Figure 7:
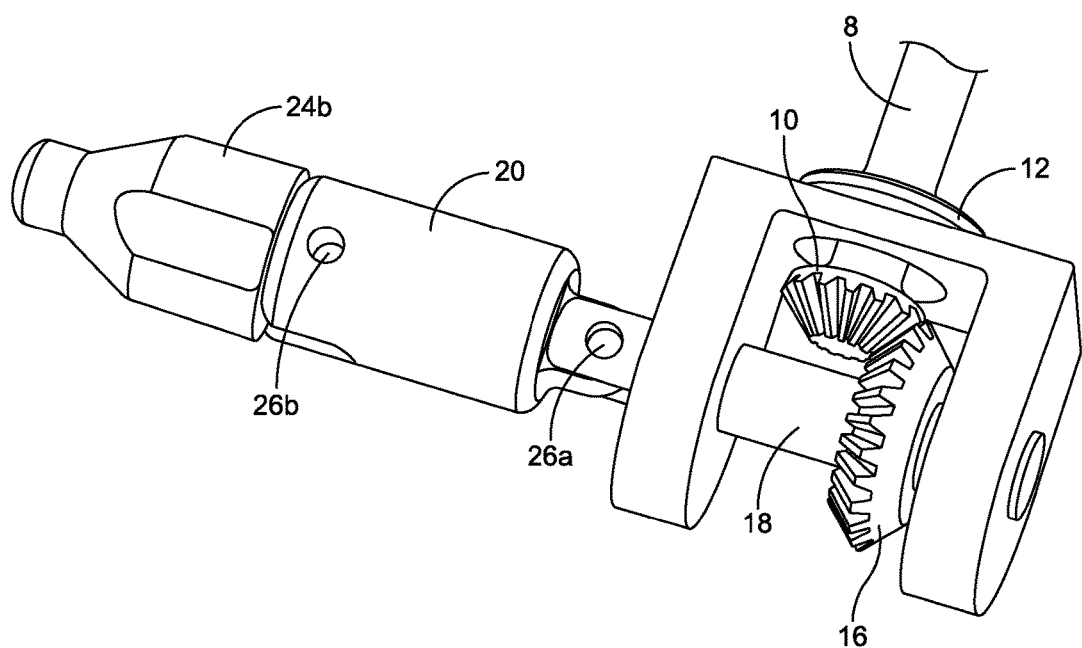
FIG. 7 illustrates a gear assembly and stem of the instrument of FIG. 4.

FIGS. 6 and 7 illustrate the modular connections 26a, 26b between the stem 18, modular extender 20, and the modular head 24. In the illustrated embodiment, the modular connections 26a, 26b comprise hinged connections that allow the modular extender 20 and/or the modular head 24 to deflect with respect to the longitudinal axis of the stem 18 while maintaining rotational coupling between the stem 18, modular extender 20, and the modular head 24. In some embodiments, the modular connections 26a, 26b comprise a fixed coupling to prevent movement of the modular head 24 and/or the modular extender 20 with respect to the stem 18. The modular connections 26a, 26b are configured to allow the modular head 24 and/or the modular extender 20 to be attached and removed from the stem 18 without needing to withdraw the geared instrument 2 from a surgical site.

Figure 8:
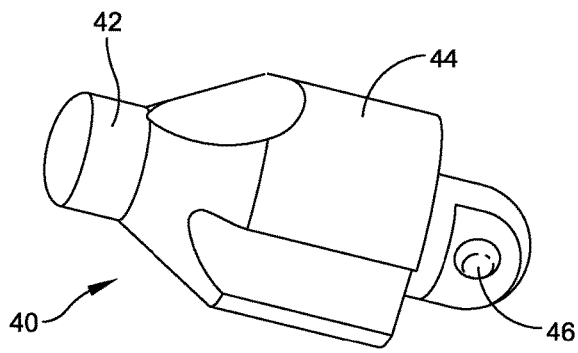
FIGS. 8-11 illustrate various embodiments of modular heads configured to couple to the instrument of FIG. 1.
Figure 9:
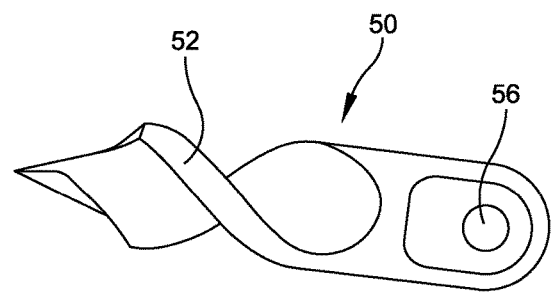

FIGS. 8-11 illustrate various example embodiments of modular heads that may be coupled to the stem 18 of the geared instrument 2. FIG. 8 illustrates an example reamer head 40. The reamer head 40 is configured to ream a hole in a bone, such as, for example, a tibia, to receive an implant therein. The reamer 40 comprises a first end having a reaming guide 42 sized and configured to fit within a pilot hole. A reaming section 44 is located proximally of the reaming guide 42. A modular connection 46 is located at a proximal end of the reamer 40. FIG. 9 illustrates an example drill head 50. The drill head 50 is configured to drill a hole, such as, for example a pilot hole, into a bone, such as a tibia. In one embodiment, the drill head 50 is configured to drill a pilot hole for the reamer head 40. The drill head 50 comprises a fluted section 52 extending longitudinally and a modular connection 56 located at a proximal end of the drill head 50.

Figure 10:
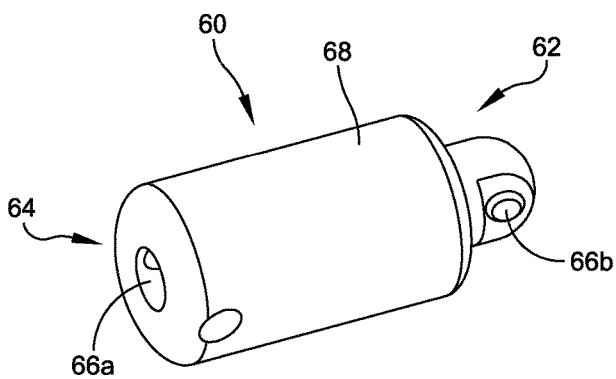

FIG. 10 illustrates one embodiment of a modular extender 60. The modular extender 60 is configured to couple between the modular head 24 and the stem 18. The modular extender 60 allows a modular head 24 to reach a greater depth within a bone. The modular extender 60 comprises a proximal end 62 defining a first modular connection 66a and a distal end 64 defining a second modular connection 66b. The first modular connection 66a is configured to couple to the stem 18. The second modular connection 66b is configured to couple to a modular head 24. The modular extender 60 comprises a cylindrical body 68 extending along a longitudinal axis to a predetermined length. Although a cylindrical body 68 is shown, it will be appreciated that the body of the modular extender 60 may have any suitable shape.

Figure 11:
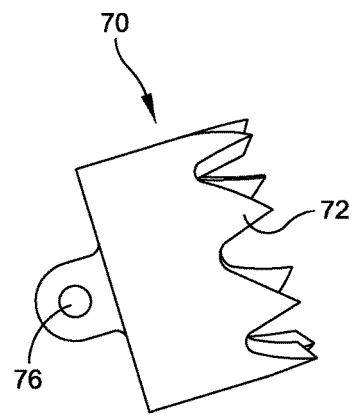

FIG. 11 illustrates one embodiment of a stem remover 70. The stem remover 70 is configured to remove bone on-growth of an implant to allow easier removal of the implant during, for example, a revision procedure. The stem remover 70 comprises a perimeter cutting head 72 sized and configured to be slightly larger than an implant stem to allow the perimeter cutting head 72 to remove bone on-growth. A modular connection 76 is located at a proximal end of the stem remover 70. Those skilled in the art will recognize that other suitable modular heads may be coupled to the geared instrument 2 for various surgical procedures. The illustrated modular heads 40, 50, 60, 70 may comprise a one or more sizes corresponding to patient-specific dimensions. For example, in some embodiments, the reamer 40 may be available in multiple sizes to allow for size differences in patients and/or to facilitate resectioning of a tibia for a larger implant.

Figure 12:
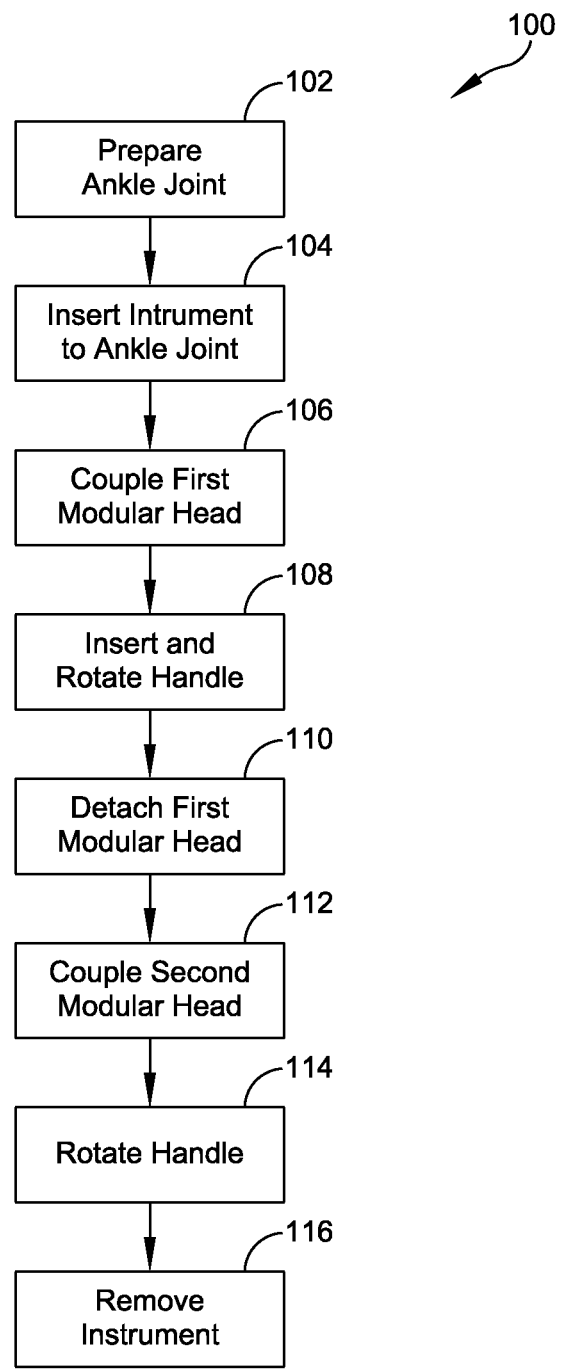
FIG. 12 is a flowchart illustrating one embodiment of a method for tibial stem reaming using the instrument illustrated in FIGS. 1-11.

FIG. 12 illustrates one embodiment of a method 100 of preparing a tibia for a total ankle replacement using the geared instrument 2 illustrated in FIGS. 1-10. In a first step 102, an ankle joint is prepared to receive the geared instrument 2. Preparation of the ankle may comprise, for example, forming an anterior incision, removing a portion of a tibia and/or a talas, and measuring for patient-specific implants. In a second step 104, the geared instrument 2 is inserted into the ankle joint (as shown in FIG. 13). The geared instrument 2 comprises a housing 14 that is sized and configured to be received within the ankle joint. The housing 14 is configured to be free-floating within the ankle joint to allow the geared instrument 2 to be arranged as needed to perform one or more operations. In some embodiments, the geared instrument 2 is arranged such that the stem 18 extends towards a tibia.

In a third step 106, a first modular head is coupled to the stem 18 of the geared instrument 2. A modular extension 20 may optionally be coupled between the modular head 24 and the stem 18. The first modular head may comprise, for example, a modular drill bit 50. In a fourth step 108, a handle 4 is inserted into the geared instrument 2 through a top opening in the housing 14. The handle 4 comprises a handle gear 10 that couples to a translation gear 16 within the housing 14. The handle 4 is rotated about a first longitudinal axis. The rotation of the handle 4 is translated to rotation of the stem 18 about a second longitudinal axis. Rotation of the stem 18 causes rotation of the first modular head. For example, a modular drill bit 50 is rotated about the second longitudinal axis to drill a pilot hole into a tibial canal.

In a fifth step 110, the first modular head is detached from the stem 18. The first modular head may be removed from the patient or may be left within the patient until completion of the procedure. In a sixth step 112, a second modular head is coupled to the stem 18. The second modular head may comprise, for example, a reamer 40. In a seventh step 114, the handle 4 is rotated about the first axis to rotate the reamer 40 about the second axis. The reamer 40 reams a stem hole in the tibia. In some embodiments, a modular extension 20 is located between the stem 18 and the reamer 40 to allow the reamer 40 to extend deeper into the tibia. In an eighth step 116, the geared instrument 2 and the modular heads are removed from the ankle joint to allow one or more implants to be attached to the ankle joint. The use of the geared instrument 2 prevents the need to form incisions other than the anterior incision.

In some embodiments, an instrument is disclosed. The instrument comprises a handle configured to rotate about a first axis, a translation gear configured to be coupled to the handle, and a stem coupled to the translation gear. The gear is configured to translate rotation of the handle about the first axis to rotation about a second axis. A stem is coupled to the gear. The stem is configured to receive a modular head. The stem is rotated about the second axis by the gear.

In some embodiments, the handle comprises a handle gear configured to couple to the translation gear.

In some embodiments, the instrument comprises a housing defining a vertical opening and a lateral opening. The translation gear is located within the housing. The stem extends longitudinally from the translation gear and through the lateral opening. The vertical opening is sized and configured to receive the handle therein.

In some embodiments, the housing is sized and configured to be received within an ankle joint.

In some embodiments, the translation gear comprises one of a bevel gear, a worm gear, a spiral bevel gear, or a hypoid gear.

In some embodiments, the instrument comprises an extender releasably coupled to the stem. The extender is configured to receive the modular head.

In some embodiments, the modular head comprises one of a reamer, a drill, or a stem remover.

In some embodiments, the first axis is perpendicular to the second axis.

In some embodiments, a surgical system is disclosed. The surgical system comprises an instrument and a modular head. The instrument comprises a handle configured to rotate about a first axis, a translation gear configured to be coupled to the handle, and a stem coupled to the translation gear. The translation gear translates rotation of the handle about the first axis to rotation about a second axis. The stem is rotated about the second axis by the gear. The modular head is coupled to the stem.

In some embodiments, the handle comprises a handle gear configured to couple to the translation gear.

In some embodiments of the surgical system, the instrument comprises a housing defining a vertical opening and a lateral opening. The translation gear is located within the housing. The stem extends longitudinally from the translation gear and through the lateral opening. The vertical opening is sized and configured to receive the handle therein.

In some embodiments, the housing is sized and configured to be received within an ankle joint.

In some embodiments, the translation gear comprises one of a bevel gear, a worm gear, a spiral bevel gear, or a hypoid gear.

In some embodiments, the surgical system comprises an extender releasably coupled between the stem and the modular head.

In some embodiments, the modular head comprises one of a reamer, a drill, or a stem remover.

In some embodiments, the first axis is perpendicular to the second axis.

In some embodiments, a method is disclosed. The method comprises locating an instrument at an ankle joint. The instrument comprises a handle configured to rotate about a first axis, a translation gear configured to be coupled to the handle, and a stem coupled to the translation gear. The translation gear is configured to translate rotation of the handle about the first axis to rotation of the stem about a second axis. The method further comprises coupling a modular head to the stem, coupling the handle to the translation gear, and rotating the handle about the first axis to rotate the modular head about the second axis to perform a first surgical procedure.

In some embodiments, prior to coupling the modular head to the stem, the method further comprises coupling an extender to the instrument and coupling the modular head to the extender.

In some embodiments the modular head comprises a first modular head and the method further comprises detaching the first modular head from the stem, coupling a second modular head to the stem, and rotating the handle about the first axis to rotate the second modular head about the second axis to perform a second surgical procedure.

In some embodiments, the modular head comprises one of a reamer, a drill, or a stem remover.

What is claimed is:

1. A method, comprising:
   forming an anterior incision to access an ankle joint;
   locating a housing of an instrument in the ankle joint, the instrument comprising a translation gear disposed within the housing and a stem coupled to the translation gear;
   coupling a modular head to the stem;
   inserting a handle into the housing and coupling the handle to the translation gear such that the translation gear translates rotation of the handle about a first axis to rotation of the stem about a second axis; and
   rotating the handle about the first axis to rotate the modular head about the second axis to perform a first surgical procedure.

2. The method of claim 1, wherein prior to coupling the modular head to the stem, the method further comprises:
   coupling an extender to the instrument; and
   coupling the modular head to the extender.

3. The method of claim 1, wherein the modular head comprises a first modular head, and wherein the method further comprises:
   detaching the first modular head from the stem;
   coupling a second modular head to the stem; and
   rotating the handle about the first axis to rotate the second modular head about the second axis to perform a second surgical procedure.

4. The method of claim 1, wherein the modular head comprises one of a reamer, a drill, or a stem remover.

* * * * *